United States Patent [19]
Brown

[11] Patent Number: 5,948,986
[45] Date of Patent: *Sep. 7, 1999

[54] MONITORING OF WAFER PRESENCE AND POSITION IN SEMICONDUCTOR PROCESSING OPERATIONS

[75] Inventor: Karl Brown, San Jose, Calif.

[73] Assignee: Applied Materials, Inc., Santa Clara, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/998,451

[22] Filed: Dec. 26, 1997

[51] Int. Cl.⁶ .......................... G01N 29/00; H02N 13/00
[52] U.S. Cl. ............................... 73/630; 361/234
[58] Field of Search .................... 73/630, 629, 597; 361/234; 367/93, 96

[56] References Cited

U.S. PATENT DOCUMENTS

| | | |
|---|---|---|
| 4,158,171 | 6/1979 | Abbe et al. . |
| 4,344,160 | 8/1982 | Gabriel et al. ............... 73/597 |
| 4,409,087 | 10/1983 | Quick ....................... 204/298 |
| 4,513,430 | 4/1985 | Vora et al. . |
| 4,603,466 | 8/1986 | Morley . |
| 4,657,621 | 4/1987 | Johnson et al. . |
| 4,697,089 | 9/1987 | Drage . |
| 4,770,590 | 9/1988 | Hugues et al. . |
| 4,819,167 | 4/1989 | Cheng et al. . |
| 4,836,733 | 6/1989 | Hertel et al. . |
| 4,875,005 | 10/1989 | Terada et al. . |
| 5,054,991 | 10/1991 | Kato . |
| 5,103,367 | 4/1992 | Horwitz et al. . |
| 5,117,121 | 5/1992 | Watanabe et al. . |
| 5,194,743 | 3/1993 | Aoyama et al. . |
| 5,208,648 | 5/1993 | Betachelder et al. . |
| 5,222,329 | 6/1993 | Yu . |
| 5,275,683 | 1/1994 | Arami et al. . |
| 5,319,216 | 6/1994 | Mokuo et al. . |
| 5,325,261 | 6/1994 | Horwitz . |
| 5,378,994 | 1/1995 | Novak et al. . |
| 5,382,311 | 1/1995 | Ishikawa et al. . |
| 5,436,790 | 7/1995 | Blake et al. . |
| 5,483,138 | 1/1996 | Shmookler et al. . |
| 5,539,323 | 7/1996 | Davis, Jr. . |
| 5,540,098 | 7/1996 | Ohsawa ....................... 73/629 |
| 5,547,539 | 8/1996 | Arasawa et al. . |
| 5,556,147 | 9/1996 | Somekh et al. . |
| 5,563,798 | 10/1996 | Berken et al. . |
| 5,606,251 | 2/1997 | Ryle et al. . |
| 5,622,693 | 4/1997 | Funatsu . |
| 5,654,508 | 8/1997 | Gibbs ....................... 73/630 |

FOREIGN PATENT DOCUMENTS

| | | |
|---|---|---|
| 63-194345 | 8/1988 | Japan . |
| 6-156624 | 6/1994 | Japan . |
| 7130830 | 5/1995 | Japan . |

*Primary Examiner*—John E. Chapman
*Attorney, Agent, or Firm*—William K. Konrad

[57] ABSTRACT

A workpiece support assembly in a processing chamber, the assembly including a support member having an upper surface to be contacted by a workpiece and a lower surface located opposite the upper surface; and a workpiece position monitoring system mounted on the lower surface and isolated from the interior of the chamber for detecting contact between the upper surface and a workpiece at each of a plurality of individual locations on the upper surface. The workpiece position monitoring system consists of a plurality of electroacoustic signal transducers mounted on the lower surface of the support member for generating acoustic waves in the support member and receiving reflected acoustic waves. The intensity of acoustic waves reflected from the upper surface is monitored to determine the position of a workpiece, such as a semiconductor wafer, on the support member.

44 Claims, 3 Drawing Sheets

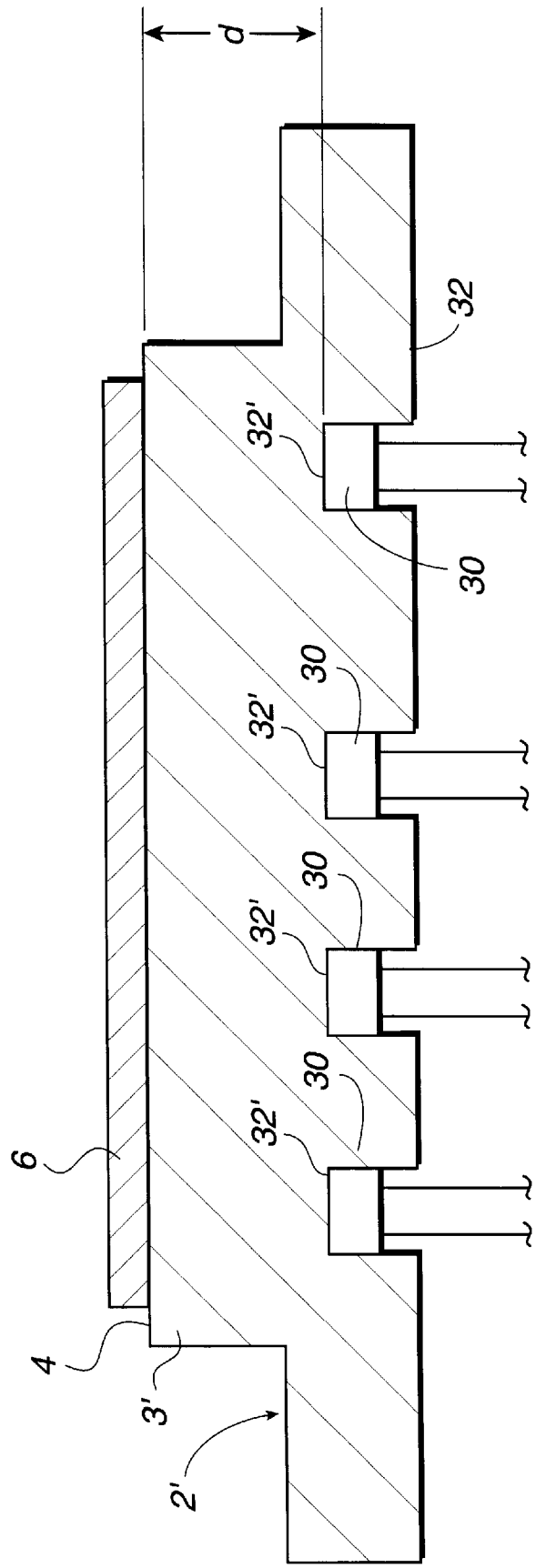

MONITORING OF WAFER PRESENCE AND POSITION IN SEMICONDUCTOR PROCESSING OPERATIONS

BACKGROUND OF THE INVENTION

The present invention relates to devices for holding semiconductor wafers and similar articles in processing apparatus.

Many types of industrial processing operations require automated transfer of articles undergoing processing between successive processing stations. An exemplary operation of this type is semiconductor wafer fabrication, in which an article in the form of a semiconductor wafer is transferred between various processing units, each unit performing a different operation. Such operations include film deposition, ion implantation, impurity diffusion, etching, etc. which are performed in a processing chamber containing a suitable atmosphere.

Each processing unit includes some type of support for securely holding the wafer in position for processing. Known supports include those that employ mechanical clamps, as disclosed in U.S. Pat. No. 4,603,466 (M. J. Morley), and those which employ electrostatic forces, as disclosed in U.S. Pat. No. 5,103,367 (Horwitz et al) as well as in patents and publications cited therein.

When articles such as semiconductor wafers are transferred from one unit to another by automated equipment, there is always the possibility of a malfunction that results in a failure to deliver an article to a support or incorrect positioning of the article on the support. Therefore, in installations of this type, it is desirable to monitor correct positioning of a wafer before the start of a processing operation.

U.S. Pat. No. 5,103,367, cited above, discloses an electrostatic chuck in which voltages are applied to electrodes to produce electrostatic attraction forces. The voltages produce a current between each electrode and a reference electrode and the amplitude of the currents increases as a wafer is brought closer to the chuck. When the wafer is sufficiently close, these currents attain an amplitude which produces a switching effect to increase the voltage applied to the electrodes, thereby substantially increasing the electrostatic attraction forces.

Monitoring of wafer proximity according to this patent appears to be only for the purpose of determining when to apply an increased holding force, and it appears to be assumed that the wafer will be automatically placed in the correct position. There does not appear to be a provision for any alarm or other fault response if the wafer does not arrive at the correct position. Moreover, there does not appear to be any indication in this patent that the proximity sensing system could provide an indication if the wafer is on the chuck but is misaligned.

If a wafer that has been placed on the surface of the chuck is somewhat warped, or bowed, then the electrostatic attraction force which must be applied to place the wafer flat against the upper surface of the chuck generally will require a higher value than that which would be required for a perfectly flat wafer. It is therefore known to produce electrostatic attraction forces which are higher than those required by a perfectly flat wafer. However, such increased electrostatic attraction forces can cause the lower surface of the wafer to become scratched, and thereby possibly produce particles which might circulate in the processing chamber and contaminate the upper surface of the wafer.

Certain electrostatic chucks which are known in the art include passages via which gas is supplied to the underside of a wafer mounted on the chuck in order to heat the wafer to processing temperature. The pressure of gas flowing through the passages may be monitored in order to determine whether a wafer is present on the chuck. Exemplary chucks of this type are marketed by Applied Materials, Inc. of Santa Clara, Calif. under the product designation PVD-ECHUCK.

Systems of this type can very reliably indicate situations in which a wafer is completely absent. However, these systems are not intended to be able to indicate that a wafer while present on the chuck is nonetheless incorrectly positioned, or has a piece broken off, or is warped so that only a portion of the wafer contacts the wafer support surface of the chuck.

Another approach is to use capacitance to detect wafer position. For example, U.S. Pat. No. 5,436,790 issued Jul. 25, 1995 describes a wafer presence and clamp condition monitoring apparatus which monitors capacitance between two electrodes embedded within a wafer support pedestal. The capacitance falls into one range with no wafer positioned upon the support surface and into a second range with a wafer in place but not clamped. Furthermore, the capacitance falls in a third range with the wafer held in place by an electrostatic chuck formed when the embedded pair of electrodes are energized with a DC voltage. The monitoring circuit senses when the capacitance of the system is in each of the ranges by converting the measured capacitance to a DC voltage that can easily be sensed and used to confirm wafer placement and clamping.

Specifically, the electrostatic chuck used in the prior art system contains a pliable surface such that when the clamping force is applied, the wafer compresses the surface material and the wafer physically moves nearer to the pedestal surface and its embedded electrodes. This physical movement of the wafer relative to the electrodes causes a change in the capacitance between the electrodes. Such pliable surface materials are typically useful primarily in low temperature semiconductor processing systems. At high temperatures, these materials tend to breakdown, outgas and/or deform. Thus, at high temperatures, an electrostatic chuck having a pliable surface may contaminate the chamber.

Ceramic electrostatic chucks that are typically used in high temperature semiconductor wafer processing are constructed of a ceramic material that becomes somewhat conductive at high temperatures (i.e., the resistivity of the material decreases with increased temperature). Specifically, when the wafer rests flush against the surface of the chuck body while chucking voltage is applied to one or more embedded electrodes, the wafer is primarily retained against the ceramic support by the Johnsen-Rahbek effect. One example of such a ceramic chuck is disclosed in U.S. Pat. No. 5,117,121 issued May 26, 1992 and incorporated herein by reference.

Ceramic chucks of this type have a hard, non-pliable surface that generally does not breakdown or deform during high temperature wafer processing.

Copending application entitled "Method and Apparatus for Wafer Detection" Ser. No. 08/873,260, filed Jun. 11, 1997, (Attorney Docket 1913) is directed to a capacitive position sensor for such high temperature chucks. However, capacitive sensors have a number of drawbacks. For example, capacitive sensors typically require that at least one electrical lead be brought into the interior of the processing chamber. Since the interior of the chamber must be isolated from the region surrounding the chamber, the need to provide a feedthrough for that lead presents additional design and fabrication complications. In addition, known capacitive sensors can sense the pressure of a wafer, but typically cannot reliably indicate if the wafer is correctly positioned.

Therefore, a need exists in the art for other systems that detect wafer presence and operate at high wafer processing temperatures.

BRIEF SUMMARY OF THE INVENTION

It is an object of the present invention to provide improved monitoring of the presence and position of a wafer on a chuck in a deposition chamber.

A more specific object of the invention is to provide indications when a wafer is present on a chuck but is incorrectly positioned and/or has a piece broken off and/or is warped.

Yet another object of the invention is to detect the position and condition of a wafer on the wafer support surface of a chuck using a system which does not physically contact the wafer and is permanently isolated from the atmosphere at the interior of the deposition chamber.

The above and other objects are achieved, according to the present invention, by a workpiece support assembly in a processing chamber, the assembly comprising a support member having an upper surface to be contacted by a workpiece and a lower surface located opposite the upper surface; and workpiece position sensor mounted on the lower surface for acoustically detecting contact between the upper surface and a workpiece at each of a plurality of individual locations on the support surface.

In the illustrated embodiment, acoustic waves are propagated through the support member from a lower surface to the upper surface at each one of a plurality of individual locations on the upper surface. The intensity of the acoustic waves reflected from each individual location on the upper surface to the lower surface may be monitored to detect wafer position at each location.

In another aspect of the invention, the workpiece support member is an electrostatic chuck which produces a workpiece holding force in response to a voltage applied to the chuck, wherein the voltage may be incrementally applied in response to the result of the monitoring procedure in order to place an initially warped workpiece flat against the upper surface of the chuck, yet minimize scratching of the workpiece.

According to preferred embodiments of the invention, the workpiece position sensor apparatus includes a plurality of electroacoustic transducers mounted on the lower surface of the workpiece support member and each producing an acoustic wave which is propagated preferentially to a respective individual location on the upper surface of the support member.

BRIEF DESCRIPTION OF THE SEVERAL VIEWS OF THE DRAWING

FIG. 1a is an elevational, cross-sectional view of a pedestal of a monitoring system in accordance with an alternative embodiment.

DETAILED DESCRIPTION OF THE INVENTION

Figure 1:
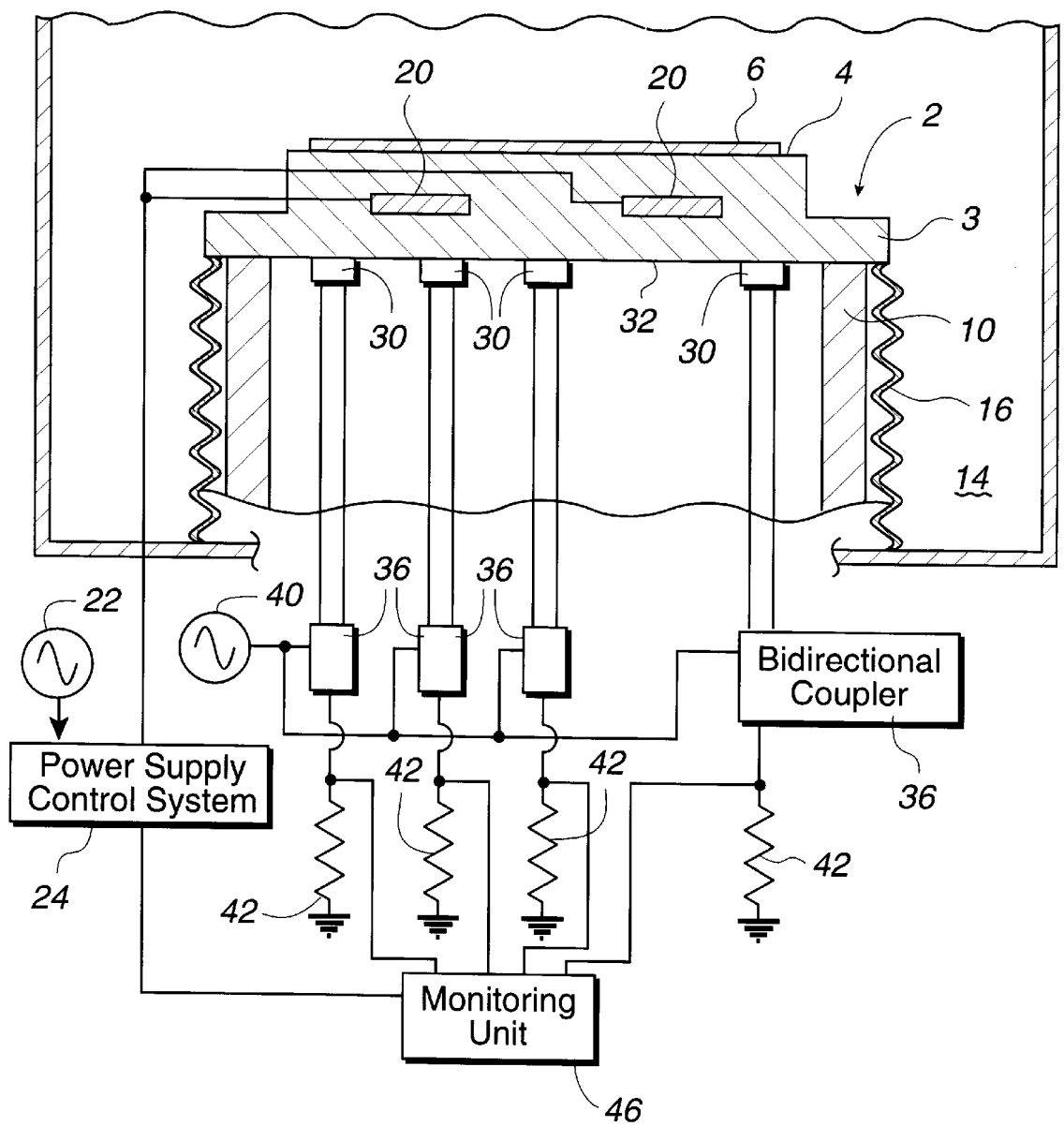
FIG. 1 is partly an elevational, cross-sectional view and partly a block circuit diagram of an electrostatic chuck equipped with a monitoring system according to the present invention.

FIG. 1 illustrates one embodiment of an electrostatic chuck assembly equipped with a monitoring system according to the invention.

The chuck assembly 2 includes a pedestal 3 preferably made of a dielectric material. The upper surface of the pedestal 3 constitutes a workpiece support and holding surface 4 intended to hold a workpiece 6, such as a silicon wafer. Pedestal 3 is mounted on a suitable support structure 10 having any appropriate form of construction and is installed within a processing chamber 14 in which workpiece 6 is to be subjected to any one of a variety of processing operations including, but not limited to, deposition and etching. Chuck 2 is coupled to chamber 14 via a bellows 16 which is provided to allow chuck 2 to be moved vertically by support system 10 while maintaining the interior of chamber 14 in a sealed condition.

A selected number of electrodes 20 is embedded within chuck 2 and are supplied with a suitable voltage, which may be a low frequency ac voltage of controlled amplitude and phase, from a power supply 22 via a suitable control system 24. Workpiece 6 is held against surface 4 by electrostatic forces that are determined essentially by the magnitude of the voltage applied to electrodes 20. All of the structure described thus far can be constituted by components which are already known in the art and/or in accordance with principles that are known in the art.

According to one aspect of the present invention, a plurality of electromechanical transducers 30 are secured to the underside, or bottom surface, 32 of the pedestal 3 of the chuck 2. Each transducer 30 may be of a type known in the art. According to one preferred embodiment, ultrasonic acoustic wave transducers, preferably of the piezoelectric type, would be employed. However, other known types, such as variable resistance, variable reluctance, moving coil, or variable capacitance types could be employed.

Transducers 30 of the illustrated embodiment are of the bidirectional, or transceiver, type, i.e. are capable of converting an alternating electrical signal into mechanical motion and converting mechanical motion into an alternating electrical signal. Mechanical motion induced in a transducer 30 which is suitably mechanically coupled to the body of pedestal 3 will generate an acoustic wave which is propagated within pedestal 3.

Each transducer 30 may be attached to bottom surface 32 in any suitable known manner capable of establishing efficient coupling between mechanical movements of the transducer and acoustic waves within pedestal 3. Such attachment can be achieved, for example, with mechanical coupling components or suitable adhesives.

Each transducer 30 is coupled via a pair of conductors to a respective bidirectional coupler 36. Each coupler 36 has an input connected to an ac power supply 40 and an output connected to a respective measuring resistor 42. Each coupler 36 is constructed in a manner known in the art to supply an alternating voltage produced by power supply 40 across the conductors connected to each transducer 30 and to supply electrical signals produced in transducer 30 via the associated conductors to a respective measuring resistor 42. Ground connections associated with power supply 40 and resistor 42 are not shown in order to simplify the illustration.

Each coupler 36 may be of the duplex type in which electrical signals can be continuously transmitted in both directions, or can be of the time division multiplexer type in which an alternating voltage is delivered from power supply 40 to each transducer 30 during a first time interval and voltages induced in each transducer 30 are supplied to a respective measuring resistor 42 during a second time interval.

The frequency of the alternating voltage provided by power supply 40 is preferably selected to produce, in pedestal 3, an acoustic wave having a wavelength substantially equal to the thickness of pedestal 3, i.e. substantially equal to the vertical distance between surfaces 4 and 32. Alternatively, a wavelength may be selected for which the thickness of the pedestal 3 is an integral multiple of the wavelength. Other wavelengths may be selected as well.

Still further, in the illustrated embodiment of FIG. 1, the lower surface 32 to which the transducers 30 are shown to be coupled, is depicted as being a generally planar surface which is the bottom-most lower surface of the dielectric pedestal 3 of the chuck 2. It should be appreciated of course that the transducers 30 may be embedded or otherwise received wholly or partially within the dielectric pedestal as shown for a pedestal 3' in FIG. 1a, for example. There, the distance d between the top surface 4 of the pedestal 3' and the lower surface 32' of the pedestal dielectric material to which a transducer 30 is coupled may be less than the overall thickness of the pedestal 3' as represented by the distance between the top surface 4 and the bottom-most surface 44 of the dielectric material of the pedestal 3'. However, in this case also, the distance d between the top surface 4 and the transducer coupling surface 32' of the dielectric material of the pedestal 3', and is again preferably equal to one wavelength (or an integral multiple of the wavelength) of the acoustic wave emitted by the transducer.

By selecting the distance from the transducer to the top surface of the pedestal to be an integral multiple of the acoustic wavelength, a resonance condition can be set up when the wafer is not in contact with the surface above the transducer. This resonance condition can be used to detect the presence or absence of the wafer above the transducer as described below.

In addition, each transducer 30 is preferably constructed to have a directional acoustic wave radiation pattern with a narrow lobe and an axis perpendicular to surfaces 4 and 32. Thus, the acoustic wave produced by a transducer 30 will interact with a portion of chuck 2 and a portion of wafer 6 at a location which is vertically aligned with the respective transducer 30. If the acoustic wave radiation, or transmission, pattern has a sufficiently high directionality, any acoustic energy cross talk between transducers will have a minimum influence on the electrical signal generated by each transducer in response to reflected acoustic energy.

Alternatively, the connection between power supply 40 and couplers 36 can be controlled in a time multiplex manner. In this case, a time slot would be assigned to each transducer 30; within an associated time slot, an alternating voltage would be conducted from supply 40 to the associated transducer 30 and an electric signal generated by reflected acoustic waves would be supplied to produce a corresponding voltage across the associated measuring resistor 42. The delivery of voltage from supply 40 to transducer 30 can take place during a first time interval and the supply of the electric signal generated by reflected acoustic waves to the associated measuring resistor 42 could be effected during successive time intervals within the associated time slot.

When an acoustic wave is propagated from a respective transducer 30, then the intensity of the acoustic energy reflected back to that transducer will be dependent on whether or not wafer 6 is in contact with the surface 4 at the individual portion of surface 4 which is associated with that transducer 30. When wafer 6 is not in contact with a portion of surface 4 associated with a respective transducer 30, substantially all of the acoustic wave energy propagated by that transducer 30 will be reflected by surface 4 back to transducer 30. When the distance from the transducer to the top surface of the pedestal coincides with an integral multiple of the acoustic wavelength, a standing wave can be maintained in a resonance condition. On the other hand, when wafer 6 is in contact with the associated portion of surface 4, a portion of the acoustic energy propagated by transducer 30 will be propagated through wafer 6 and will be reflected from the upper surface of wafer 6 back to transducer 30. This energy will arrive at transducer 30 with a phase shift relative to the energy reflected from surface 4, resulting in a variation in the peak value (usually an attenuation) of the alternating electrical signal conducted from transducer 30 to measuring resistor 42.

As a result, when the alternating voltage produced by power supply 40 has a constant magnitude, the magnitude of the voltage across a measuring resistor 42 will depend on whether or not wafer 6 is in contact with the respective portion, or location, of surface 4.

In a typical system to which the invention is to be applied, pedestal 3 of chuck 2 will have a thickness in the range of 5–15 mm, while wafer 6 will have a thickness of the order of 1 mm. The thickness of wafer 6 will be a sufficiently large fraction of the thickness of pedestal 3 to assure that the difference between the magnitude of the voltage across measuring resistor 42 when wafer 6 is in contact with an associated portion of surface 4 and the magnitude of the voltage across resistor 42 when wafer 6 is not in contact with that portion of surface 4 will be sufficiently large to allow the desired detection to be achieved.

The voltages produced across all of measuring resistors 42 are supplied to a monitoring unit 46 which determines the magnitude of the voltage across each measuring resistor 42. Within monitoring unit 46, each magnitude determination can be compared with the voltage value which will exist if wafer 6 is in contact with the respective portion of surface 4.

Based on this comparison, monitoring unit 46 can produce any suitable output indicating either that the entirety of wafer 6 is in proper contact with surface 4, or identifying that portion of wafer 6 which is not in proper contact with surface 4. This information can be provided in the form of a display, or an alarm signal, or a signal for controlling the magnitude of the voltage supplied to electrodes 20 via control system 24. In the latter case, monitoring unit 46 may determine that wafer 6 is in contact with one or more, but less than all, of the individual portions, or locations, of surface 4. When such a determination is made, it can be initially assumed that wafer 6 is warped and the signal applied by monitoring unit 46 to control system 24 will act to increase the voltage applied to electrodes 20. This increase can occur in steps, alternating with measurement of the voltages across measuring resistors 42, causing the voltage applied to electrodes 20 to be increased incrementally until the voltages across all resistors 42 indicate that all portions of wafer 6 are in contact with surface 4.

By this procedure, the electrostatic attraction force produced by the voltage on electrodes 20 can be adjusted to the value required to properly position wafer 6 without imposing unnecessarily high attraction forces which could produce scratches in the lower surface of wafer 6.

Monitoring unit 46 can further be constructed to allow the voltage applied to electrode 20 to rise only to a preselected maximum value. If this value is reached, and the voltages across resistors 42 continue to indicate that some portion of wafer 6 is not in contact with surface 4, it can be concluded that a portion of wafer 6 has broken off, in which case the system should be shutdown to retrieve the wafer pieces.

It will be appreciated from the description presented above that monitoring unit 46 can be constructed in accordance with principles well-known in the art since this unit need do nothing more than compare the voltage across each measuring resistor 42 with a reference voltage and provide an appropriate indication of the relation between the compared values for each transducer 30. Any appropriate logical linkage can be provided between the resulting comparison values to derive the control signal for controlling system 24.

It should be appreciated that there are a number of specific uses that can be made of the signals, in addition to providing an indication that a wafer is in the proper position and is unbroken. For example, if the readings supplied to control unit 46 were stored, then successive readings from these transducers could be monitored to provide information about changes in the signals from the individual transducers over a period of time. Such information could be used to determine whether a transducer must be replaced, or whether the chuck itself must be replaced or repaired. In those embodiments in which the chucking force may be controlled individually over various locales of the chuck, the sensor information can be used to determine whether the chucking force should be modified at one or more individual locations.

Figure 2:
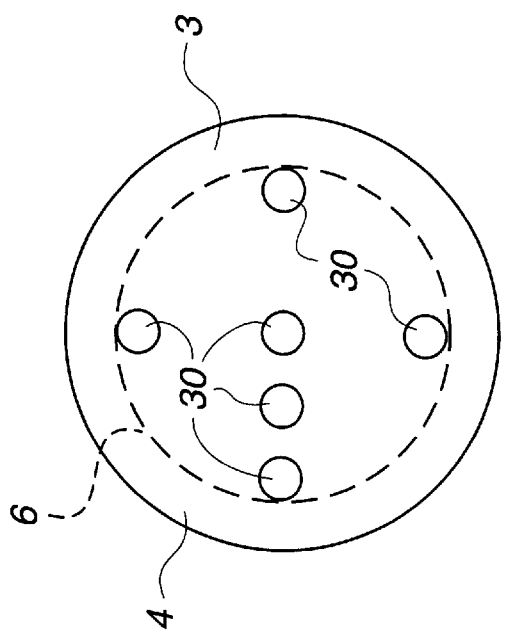
FIG. 2 is a bottom plan view of the chuck shown in FIG. 1.

FIG. 2 is a bottom plan view illustrating one suitable arrangement of transducers 30. According to this embodiment, four of the transducers 30 are located directly opposite the expected location of the periphery of a wafer 6 and are equispaced about that periphery. One of the transducers 30 may be located directly opposite the center of wafer 6 and a further transducer 30 may be located opposite a location substantially midway between the center and periphery of wafer 6 as shown. It will be appreciated that a wide variety of other transducer position arrangements is possible and that the total number of transducers employed can also be varied.

Figure 5:
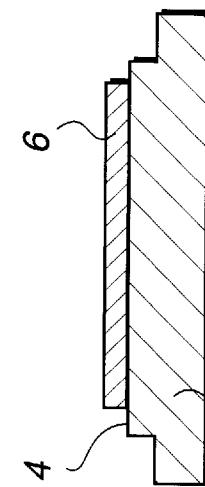
FIGS. 3, 4 and 5 are elevational, cross-sectional detail views showing three different unsatisfactory wafer conditions which can be detected according to the present invention.
Figure 4:
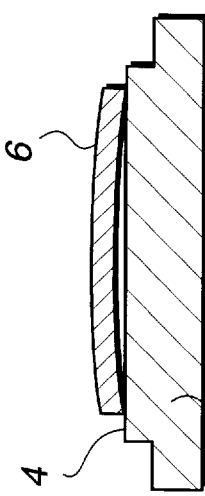
Figure 3:
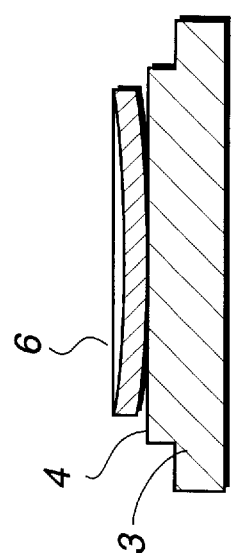

FIGS. 3, 4 and 5 are elevational, cross-sectional detail views illustrating three unsatisfactory situations which can be detected in accordance with the present invention.

FIG. 3 illustrates a situation in which wafer 6 is warped so that its upper surface has a concave curvature. In this case, the signal from the transducer 30 opposite the center of surface 4 will indicate that a wafer is present, while some or all of the transducers 30 opposite locations at the periphery of surface 4 will indicate that a wafer is not present.

Conversely, in the situation illustrated in FIG. 4, where wafer 6 is warped so that its bottom surface is concave, the signal from transducer 30 opposite the center of surface 4 will provide an indication that a wafer is not present, while signals from transducers 30 opposite locations at the periphery of surface 4 may indicate that wafer 6 is present.

FIG. 5 illustrates a situation in which a piece has broken off from the left-hand edge of wafer 6. In this case, the output signal from one transducer 30 opposite a location at the periphery of surface 4 will indicate that wafer 6 is not present.

It may be possible to correct the situations illustrated in FIGS. 3 and 4 by increasing the electrostatic holding force produced by electrodes 20 (FIG. 1). The situation illustrated in FIG. 5 cannot, of course, be corrected. In this situation, a conclusion that a piece has broken off from wafer 6 (or that a transductor has broken) may be reached if the output signal from only one peripheral transducer 30 indicates that a wafer is not present or if the voltage applied to electrodes 20 has been increased to the maximum permissible value, at which time the output signal from the one peripheral transducer 30 will continue to indicate that wafer 6 is not present.

In addition, it will be apparent that even if wafer 6 is perfectly flat and unbroken, but has been improperly positioned on surface 4, this condition can be detected by the detecting arrangement according to the present invention.

It will thus be seen that a position detecting arrangement according to the present invention permits detection of a variety of unsuitable wafer positioning situations without requiring any special measures to maintain the sealed condition of the interior of a processing chamber.

Although the pedestal 3 is described as being preferably made of a dielectric material, it is understood that other types of materials including metallic materials may be used as well. It is preferred that the pedestal material be a solid through which waves such as ultrasonic waves will readily propagate without excessive attenuation. Thus, the pedestal material should be at least partially transparent to the waves being emitted and received by the sensor.

While particular embodiments of the present invention have been shown and described, it will be apparent to those skilled in the art that changes and modifications may be made without departing from this invention in its broader aspects and, therefore, the aim in the appended claims is to cover all such changes and modifications as fall within the true spirit and scope of this invention.

What is claimed is:

1. A workpiece support assembly in a processing chamber, said assembly comprising:
   a support member having an upper surface to be contacted by a workpiece and a lower surface located opposite said upper surface; and
   electromechanical workpiece position sensing means mounted on said lower surface for detecting contact between said upper surface and a workpiece at each of a plurality of individual locations on said upper surface.

2. The assembly according to claim 1 wherein said electromechanical workpiece position sensing means comprise a plurality of electroacoustic signal transducers each mounted on said lower surface opposite a respective one of the individual locations on said upper surface for converting an alternating electrical input signal into acoustic wave energy which is propagated in said support member and for converting acoustic wave energy reflected to said transducer into an electrical output signal.

3. The assembly according to claim 2 wherein each said transducer is a piezoelectric transducer.

4. The assembly according to claim 3 wherein said workpiece position sensing means further comprise an ac electrical signal source, a plurality of ac electrical signal sensing elements and a plurality of bidirectional couplers each connected to said electrical signal source, a respective one of said transducers and a respective one of said signal sensing elements for conducting an electrical signal from said signal source to said respective one of said transducers and for conducting an electrical signal from said respective one of said transducers to said respective one of said signal sensing elements.

5. The assembly according to claim 4 wherein each of said signal sensing elements is a measuring resistor.

6. The assembly according to claim 5 further comprising means for applying a force to the workpiece to hold the workpiece in contact with said upper surface of said support member.

7. The assembly according to claim 6 wherein the force applied by said means for applying a force to the workpiece is an electrostatic force which is produced in response to a voltage and is proportional to the voltage.

8. The assembly according to claim 7 further comprising means for varying the voltage in response to the electrical output signals from said transducers.

9. The assembly according to claim 8 wherein said upper surface of said support member has a workpiece support region, said workpiece support region has a center and a periphery, and said plurality of transducers include a first transducer which is mounted opposite said center of said support region.

10. The assembly according to claim 9 wherein said plurality of transducers include at least one second transducer which is mounted opposite said periphery of said support region.

11. The assembly according to claim 9 wherein said plurality of transducers include a plurality of second transducers which are mounted opposite respective individual locations spaced apart about said periphery of said support.

12. The assembly according to claim 11 wherein said plurality of transducers include at least one third transducer which is mounted opposite a location that is between said center and said periphery of said upper surface.

13. The assembly according to claim 2 wherein said upper surface of said support member has a workpiece support region, said workpiece support region has a center and a periphery, and said plurality of transducers include a first transducer which is mounted opposite said center of said support region.

14. The assembly according to claim 13 wherein said plurality of transducers include at least one second transducer which is mounted opposite said periphery of said support region.

15. The assembly according to claim 13 wherein said plurality of transducers include a plurality of second transducers which are mounted opposite respective individual locations spaced apart about said periphery of said support.

16. The assembly according to claim 15 wherein said plurality of transducers include at least one third transducer which is mounted opposite a location that is between said center and said periphery of said upper surface.

17. The assembly of claim 2 wherein said support member is at least partially transparent to said acoustic wave energy.

18. A workpiece support assembly in a processing chamber, said assembly comprising:
a support member having an upper surface to be contacted by a workpiece and a lower surface located opposite said upper surface; and
a plurality of electroacoustic signal transducers each mounted on said lower surface for detecting contact between said upper surface and a workpiece at a respective one of a plurality of individual locations on said upper surface, each of said electroacoustic signal transducers being mechanically coupled to said support member.

19. A method for monitoring the position of a workpiece on a workpiece support member in a processing chamber, the support member having an upper surface to be contacted by a workpiece and a lower surface located opposite said upper surface, said method comprising:
propagating acoustic waves within the support member from the lower surface to the upper surface at each one of a plurality of individual locations on the upper surface; and
monitoring the intensity of acoustic waves reflected from each individual location on the upper surface to the lower surface.

20. The method according to claim 19 wherein:
said step of propagating acoustic waves comprises applying an alternating electrical signal to at least one of a plurality of electroacoustic transducers mounted on the lower surface of the support member; and
said step of monitoring comprises measuring the electrical signal produced by each transducer when acoustic waves are reflected to the lower surface of the support member.

21. The method according to claim 20 wherein each electroacoustic transducer is a piezoelectric transducer.

22. The method according to claim 19 wherein the support member is an electrostatic chuck, and wherein said method further comprises:
applying a voltage to the force to the electrostatic chuck for imposing a holding force on the workpiece which is proportional to the voltage; and
adjusting the voltage in response to the result produced in said monitoring step.

23. The assembly according to claim 18 wherein each of said electroacoustic signal transducers is mounted on said lower surface opposite a respective one of said individual locations on said upper surface to convert an alternating electrical input signal into acoustic wave energy which is propagated in said support member and to convert acoustic wave energy reflected to said transducer into an electrical output signal.

24. The assembly according to claim 23 wherein each said transducer is a piezoelectric transducer.

25. The assembly according to claim 24 further comprising an ac electrical signal source, a plurality of ac electrical signal sensing elements and a plurality of bidirectional couplers each connected to said electrical signal source, a respective one of said transducers and a respective one of said signal sensing elements for conducting an electrical signal from said signal source to said respective one of said transducers and for conducting an electrical signal from said respective one of said transducers to said respective one of said signal sensing elements.

26. The assembly according to claim 25 wherein each of said signal sensing elements comprises a measuring resistor.

27. The assembly according to claim 18 further comprising a clamp positioned to apply force to the workpiece to hold the workpiece in contact with said upper surface of said support member.

28. The assembly according to claim 27 wherein the force applied by said clamp to the workpiece is an electrostatic force which is produced in response to a voltage and is proportional to the voltage.

29. The assembly according to claim 28 further comprising a circuit for varying the voltage in response to the electrical output signals from said transducers.

30. The assembly according to claim 18 wherein said upper surface of said support member has a workpiece support region, said workpiece support region has a center and a periphery, and said plurality of transducers include a first transducer which is mounted opposite said center of said support region.

31. The assembly according to claim 30 wherein said plurality of transducers include at least one second transducer which is mounted opposite said periphery of said support region.

32. The assembly according to claim 30 wherein said plurality of transducers include a plurality of second transducers which are mounted opposite respective individual locations spaced apart about said periphery of said support.

33. The assembly according to claim 32 wherein said plurality of transducers include at least one third transducer which is mounted opposite a location that is between said center and said periphery of said upper surface.

34. The method according to claim 20 wherein said alternating electrical signal applying step comprises using a bidirectional coupler to conduct an electrical signal from a signal source to a respective one of said transducers, and wherein said monitoring step comprises using a bidirectional coupler to conduct an electrical signal output by a respective one of said transducers to a respective signal sensing element.

35. The method according to claim 34 wherein each of said signal sensing elements comprises a measuring resistor.

36. The method according to claim 35 further comprising applying a force to the workpiece to hold the workpiece in contact with said upper surface of said support member.

37. The method according to claim 36 wherein said force applying step comprises applying a voltage to an electrostatic clamp which applies a force to the workpiece which is proportional to the applied voltage.

38. The method according to claim 37 wherein said electrostatic force applying step includes varying the applied voltage in response to the electrical output signals from said transducers.

39. The method according to claim 20 wherein said upper surface of said support member has a workpiece support region, said workpiece support region has a center and a periphery, and said plurality of transducers include a first transducer which is mounted opposite said center of said support region.

40. The method according to claim 39 wherein said plurality of transducers include at least one second transducer which is mounted opposite said periphery of said support region.

41. The method according to claim 39 wherein said plurality of transducers include a plurality of second transducers which are mounted opposite respective individual locations spaced apart about said periphery of said support.

42. The method according to claim 40 wherein said plurality of transducers include at least one third transducer which is mounted opposite a location that is between said center and said periphery of said upper surface.

43. A workpiece support assembly in a processing chamber, said assembly comprising:

a support member having an upper surface to be contacted by a workpiece and a lower surface located opposite said upper surface, said upper surface contacted by said workpiece defining a workpiece support region which has a center and a periphery, said support member being at least partially transparent to acoustic signals;

a plurality of piezoelectric transducers each mounted on said lower surface for detecting contact between said upper surface and a workpiece at a respective one of a plurality of individual locations on said upper surface, each of said electroacoustic signal transducers converting an alternating electrical input signal into acoustic wave energy which is propagated in said support member and converting acoustic wave energy reflected to said transducer into an electrical output signal, each said transducer being mechanically coupled to said support member at a plurality of individual locations on said lower surface opposite said upper surface individual locations, wherein said plurality of upper surface individual locations include locations positioned at said center and said periphery of said workpiece support region, and locations intermediate said center and said periphery of said workpiece support region; and a variable force clamp positioned to clamp a workpiece to said workpiece support region at a force level responsive to a clamp input signal, said clamp input signal being responsive to said transducer output signals.

44. A method for monitoring the position of a workpiece on a workpiece support member in a processing chamber, the support member having an upper surface to be contacted by a workpiece and a lower surface located opposite said upper surface, said upper surface contacted by said workpiece defining a workpiece support region which has a center and a periphery, said support member being at least partially transparent to acoustic signals, said method comprising:

applying alternating electrical signals to a plurality of piezoelectric transducers mounted on the lower surface of the support member to propagate acoustic waves within the support member from the lower surface to the upper surface at each one of a plurality of individual locations on the upper surface, each said transducer being mechanically coupled to said support member at a plurality of individual locations on said lower surface opposite said upper surface individual locations, wherein said plurality of upper surface individual locations include locations positioned at said center and said periphery of said workpiece support region, and locations intermediate said center and said periphery of said workpiece support region;

measuring the electrical signals produced by each transducer when acoustic waves are reflected to the lower surface of the support member to monitor the intensity of acoustic waves reflected from each individual location on the upper surface to the lower surface; and applying a clamp input signal to a variable force clamp positioned to clamp a workpiece to said workpiece support region at a force level responsive to said clamp input signal, said clamp input signal being responsive to said transducer output signals.

* * * * *